United States Patent [19]

Priegnitz

[11] 4,234,520
[45] Nov. 18, 1980

[54] PROCESS FOR THE SEPARATION OF ISOMERS OF CHLORONITROBENZENE

[75] Inventor: James W. Priegnitz, Elgin, Ill.

[73] Assignee: UOP Inc., Des Plaines, Ill.

[21] Appl. No.: 30,407

[22] Filed: Apr. 16, 1979

Related U.S. Application Data

[63] Continuation-in-part of Ser. No. 14,656, Feb. 23, 1979.

[51] Int. Cl.$^3$ ............................................... C07C 79/12
[52] U.S. Cl. ..................................... 568/937; 210/670
[58] Field of Search ................ 260/646; 210/24, 30 R

[56] References Cited

U.S. PATENT DOCUMENTS

| | | | |
|---|---|---|---|
| 2,985,589 | 5/1961 | Broughton et al. | 210/34 |
| 3,558,732 | 1/1971 | Neuzil | 585/528 |
| 3,840,610 | 10/1974 | Hedge | 585/831 |

OTHER PUBLICATIONS

De Rossef et al., "Separation of Pinene Isomers", Chem. Abstracts, vol. 82 (1975) 73245m.
Chmielowiec et al., "Usefulness of Ion Exchange Resins ...", Chem. Abstracts. vol. 85 (1976) 85:136947h.
Suzuki et al., "Separation of Cresol Isomers", Chem. Abstracts, vol. 85 (1976), 85:77876c.

*Primary Examiner*—Leland A. Sebastian
*Attorney, Agent, or Firm*—James R. Hoatson, Jr.; Louis A. Morris; William H. Page, II

[57] ABSTRACT

An adsorptive separation process for separating the ortho, meta and para isomers of chloronitrobenzene from a feed mixture comprising said isomers, which process comprises contacting the feed mixture in a first adsorption stage with a certain selected adsorbent, selectively adsorbing therein substantially all of the orthochloronitrobenzene to the substantial exclusion of the other isomers and thereafter recovering high-purity orthochloronitrobenzene, passing the unadsorbed isomers to a second adsorption stage where they are contacted with another selected adsorbent, selectively adsorbing therein substantially all of one of the isomers and thereafter recovering in high purity that isomer as well as the isomer unadsorbed in the second stage. A desorption step may be used to desorb the adsorbed isomers in each stage.

9 Claims, 1 Drawing Figure

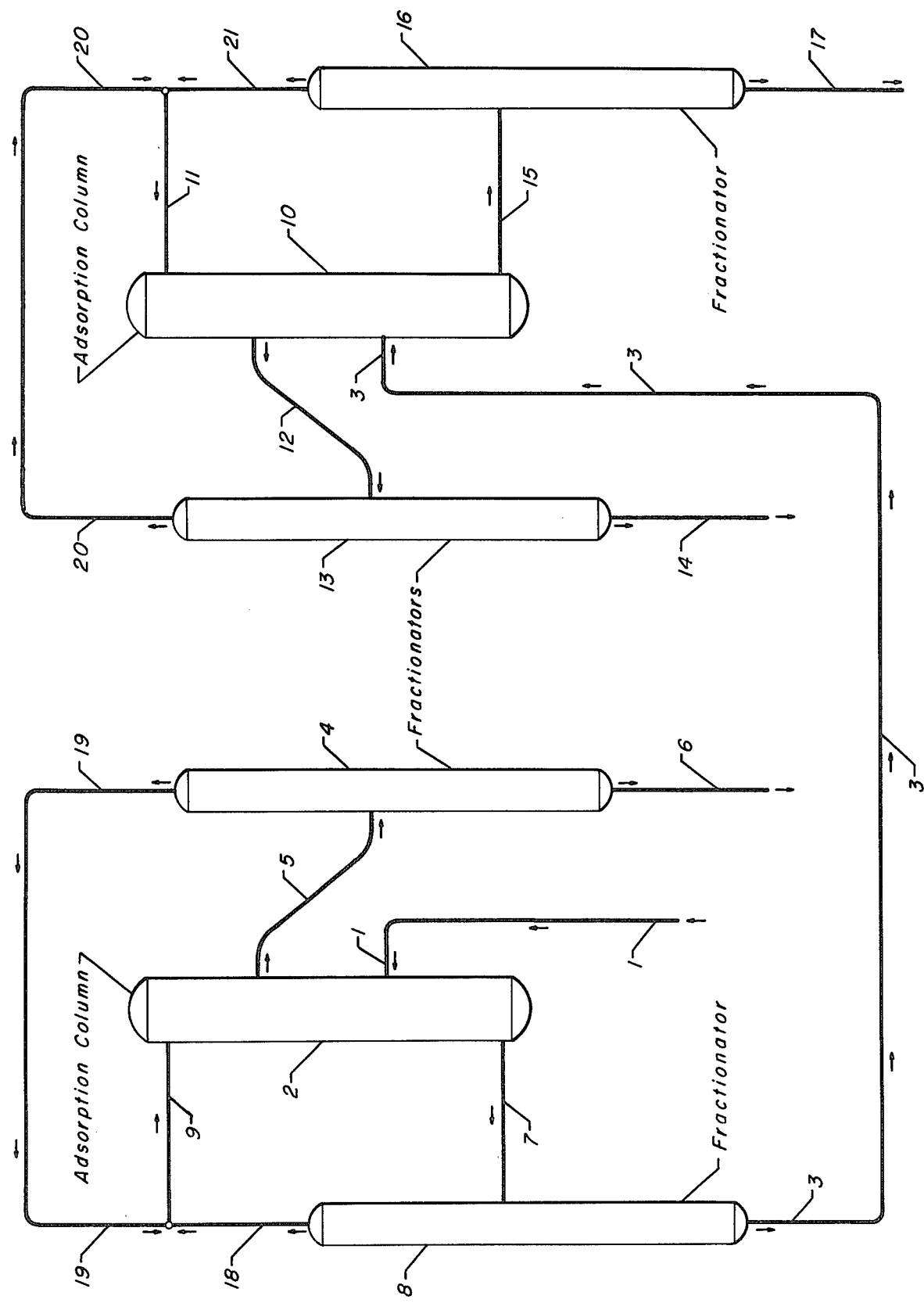

PROCESS FOR THE SEPARATION OF ISOMERS OF CHLORONITROBENZENE

REFERENCE TO PRIOR RELATED APPLICATION

This application is a continuation-in-part of my prior, copending application Ser. No. 14,656 filed Feb. 23, 1979. All of the teachings of this prior application are specifically incorporated herein by reference.

BACKGROUND OF THE INVENTION

1. Field of the Invention

The field of art to which the claimed invention pertains is solid-bed adsorptive separation. More specifically, the claimed invention relates to a process for the separation of the ortho, meta and para isomers of chloronitrobenzene from a feed mixture comprising those isomers, which process employs solid adsorbent.

2. Description of the Prior Art

The chloronitrobenzenes are important starting material for the manufacture of azo and sulfur dyes and they also find application in the synthesis of fungicides, preservatives, photochemicals, and pharamaceuticals.

Chloronitrobenzenes are prepared commercially by nitrating chlorobenzene. Chlorobenzene is nitrated at 40°–70° C. with mixed acid (52.5% $H_2SO_4$, 35.5% $HNO_3$ and 12% $H_2O$). The nitration product is a mixture of 34% o-chloronitrobenzene, 65% p-chloronitrobenzene and 1% m-chloronitrobenzene.

The methods known to the art for separating the chloronitribenzene isomers of the nitration product mixture are complicated and costly. The washed and neutralized reaction mixture must first be cooled to 16° C. and is held at this temperature which is just above the eutectic point of the mixture. Approximately half of the material crystallizes as the pure para isomer and is separated from the mother liquor. The liquid mixture must then be carefully fractionated in efficient columns to separate the isomers. The first fraction is p-chloronitrobenzene with the meta isomer, the second is mainly the para compound and the third, obtained by distillation without the column, is essentially o-chloronitrobenzene. These distillates are finally fractionally crystallized with very small amounts of methanol to separate the essentially ortho and para isomers. The noncrystalizing liquors and methanol solutions are recycled and the meta isomer is obtained by periodic concentration and separation.

Other no less complicated and costly methods known to be used for separating the ortho and para isomers from the mother liquor from the first crystallization are (a) by fractional crystallization in ethanol, (b) by the addition of 1,4-dichlorobenzene, which breaks the eutectic mixture and permits the separation of the isomers, and (c) by removing the o-chloronitrobenzene by the formation of o-nitrodiphenylamine with aniline and an alkali metal carbonate at 200° C.; the unreacted para isomer is purified by distillation.

It is well known in the separation art that certain crystalline aluminosilicates can be used to separate hydrocarbon species from mixtures thereof. The separation of normal paraffins from branched chained paraffins for example can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat. Nos. 3,265,750 and 3,510,423, for example, disclose processes in which larger pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267 a particular zeolite is used to separate specific alkyl-substituted naphthalenes. In processes described in U.S. Pat. Nos. 3,558,732; 3,686,342 and 3,997,620 adsorbents comprising particular zeolites are used to separate para-xylene from feed mixtures comprising para-xylene and at least one other xylene isomer by selectively adsorbing para-xylene over the other xylene isomers. In the last mentioned processes the adsorbents used are para-xylene selectives; para-xylene is selectively adsorbed and recovered as an extract component while the rest of the xylenes and ethylbenzenes are all relatively unadsorbed with respect to para-xylene and are recovered as raffinate components. Also, in the last mentioned processes the adsorption and desorption may be continuously in a simulated moving bed countercurrent flow system, the operating principles and sequence of which are described in U.S. Pat. No. 2,985,589.

I have discovered that the problems and shortcomings of the known methods of separation of chloronitrobenzene isomers as described above can be avoided by the application of principles, involving the use of zeolites to separate individual hydrocarbon isomers, to the separation of chloronitrobenzene isomers. My invention comprises the use of specific zeolites, for separation of the isomers of chloronitrobenzene.

SUMMARY OF THE INVENTION

It is, accordingly, a broad objective of my invention to provide a process for the separation of high-purity isomers of chloronitrobenzene at high recoveries from a feed mixture comprising the ortho, meta and para isomers of chloronitrobenzene.

In brief summary, my invention is a process for separating the ortho, meta and para isomers of chloronitrobenzene from a feed mixture comprising said isomers. The process comprises first contacting in a first adsorption stage at adsorption conditions the feed mixture with an adsorbent comprising a type X or type Y zeolite containing at the exchangeable cationic sites one or more cations selected from the group consisting of Groups IA, IIA and the transition metals of the Periodic Table of Elements. The ortho-isomers are selectively adsorbed to the substantial exclusion of the meta and para isomers. High purity ortho-chloronitrobenzene is recovered as a first extract product and the meta and para isomers as a raffinate stream. The raffinate stream is then contacted in a second adsorption stage at adsorption conditions with an adsorbent selective for either the meta or para isomer and comprising a type X or type Y zeolite containing at the exchangeable cationic sites one or more cations selected from the group consisting of Groups IA, IIA and the transition metals of the Periodic Table of Elements. The meta or para isomers is selectively adsorbed as the selected isomer to the substantial exclusion of the non-selected isomer. High purity selected isomer is recovered as a second extract product and high purity non-selected isomer as a raffinate product.

Other objectives and embodiments of my invention encompass details about feed mixtures, adsorbents, desorbent materials and operating conditions all of which are hereinafter disclosed in the following discussion of each of the facets of the present invention.

DESCRIPTION OF THE INVENTION

The type X and type Y crystalline aluminosilicates or zeolites herein contemplated are described as a three-dimensional network of fundamental structural units consisting of silicon-centered $SiO_4$ and aluminum-centered $AlO_4$ tetrahedra interconnected by a mutual sharing of apical oxygen atoms. The space between the tetrahedra is occupied by water molecules and subsequent dehydration of partial dehydration results in a crystal structure interlaced with channels of molecular dimension.

Thus, the crystalline aluminosilicates are often referred to as molecular sieves and separations performed with molecular sieves are generally thought to take place by a physical "sieving" of smaller from larger molecules appearing in the feed mixture. In the separation of aromatic hydrocarbon isomers, however, the separation of the isomers apparently occurs because of differences in electrochemical attraction of the different isomers and the adsorbent rather than on pure physical size differences in the isomer molecules.

In hydrated form, the preferred crystalline aluminosilicates generally encompass those zeolites represented by the formula 1 below:

$$M_{2/n}O: Al_2O_3 \cdot wSiO_2 \cdot yH_2O \qquad \text{Formula 1}$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The cations may be any one of a number of cations which will hereinafter be described in detail.

Adsorbents comprising the type X structured and type Y structured zeolites are especially preferred for the adsorptive separation of isomers of this invention. These zeolites are described and defined in U.S. Pat. Nos. 2,882,244 and 3,120,007 respectively. The terms "type X structured" and "type Y structured" zeolites as used herein shall include all zeolites which have general structures as represented in the above two cited patents.

The type X structured zeolite in the hydrated or partially hydrated form can be represented in terms of mole oxides as shown in Formula 2 below:

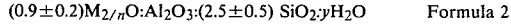

$$(0.9 \pm 0.2)M_{2/n}O:Al_2O_3:(2.5 \pm 0.5) SiO_2 \cdot yH_2O \qquad \text{Formula 2}$$

where "M" represents at least one cation having a valence of not more than 3, "n" represents the valence of "M", and "y" is a value up to about 9 depending upon the identity of "M" and the degree of hydration of the crystal. The cation "M" may be one or more of a number of cations such as the hydrogen cation, the alkali metal cation, or the alkaline earth cations or other selected cations, and is generally referred to as an exchangeable cationic site.

The type Y structured zeolite in the hydrated or partially hydrated form can be similarly represented in terms of mole oxides as in Formula 3 below:

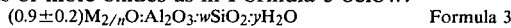

$$(0.9 \pm 0.2)M_{2/n}O:Al_2O_3 \cdot wSiO_2 \cdot yH_2O \qquad \text{Formula 3}$$

where "M" is at least one cation having a valence of not more than 3, "n" represents the valence of "M", "w" is a value greater than about 3 up to 8, and "y" is a value up to about 9 depending upon the identity of "M" and the degree of hydration of the crystal.

The term "type X zeolite" and "type Y zeolite" as employed herein shall refer not only to type X structured and type Y structured zeolites containing sodium cations as the cation "M" indicated in the formulas above but also shall refer to those containing other additional cations such as cations included in Groups IA, IIA and the transition metals of the Periodic Table of Elements. Typically both the type X and type Y structured zeolites as initially prepared and as used as a base material for the special adsorbent described herein are predominantly in the sodium form. The term "exchanged cationic site" generally refers to the site in the zeolite occupied by the cation "M". This cation, usually sodium, can be replaced or exchanged with other specific cations, such as those mentioned above, depending on the type of the zeolite to modify characteristics of the zeolite.

The term "base material" as used herein shall refer to a type X or type Y zeolite-containing starting material used to make the special adsorbent described below. Generally the base material will be in the form of particles such as extrudates, aggregates, tablets, pills, macrospheres, or granules produced by grinding any of the above to a desired size range. The type X or type Y zeolite can be present in the base material in concentrations generally ranging from about 75 wt. % to about 98 wt. % of the base material based on a volatile free composition. The remaining material in the base material generally comprises amorphous silica or alumina or both which is present in intimate mixture with the zeolite material. This amorphous material may be an adjunct of the manufacturing process of the type X or type Y zeolite (for example, intentionally incomplete purification of the zeolite during its manufacture) or it may be added to the relatively pure zeolite to aid in forming or agglomerating particles of the zeolite.

One example of a base material is commercially available nominal 1/16 inch extrudate comprising 13X zeolite and a minor amount of amorphous material as binder. This base material is primarily in the sodium form; that is, the cation represented as "M" in Formula 2 above is primarily sodium. By chemical analysis the $Na_2O/Al_2O_3$ ratio of this base material is usually about 0.7 or less and can typically be about 0.6. This, of course, is less than the $0.9 \pm 0.2$ indicated in Formula 2 above. Other cations such as H+ and any of the Group IIA metal cations may be present, primarily as impurities, to supply the remainder of the cations needed for chemical balance and to meet the $0.9 \pm 0.2$ $Na_2O/Al_2O_3$ ratio. The silica to alumina ratio of this starting material by x-ray determination is about 2.5 and the same ratio by chemical analysis is about 2.6. Normally, the base material, whether in the extrudate or pellet form, is granulated to a particle size range of about 20-40 mesh (Standard U.S. Mesh) before the first ion exchange step is begun. This is approximately the desired particle size of the finished adsorbent.

I have found that type X or type Y zeolites containing a cation selected from the group consisting of Groups IA, IIA and the transition metals of the Periodic Table of Elements are suitable for separation in a two stage system of the isomers of chloronitrobenzene from a feed mixture comprising all three of said isomers. Particularly preferred adsorbents for both stages are those comprising type X or type Y zeolite containing potassium cobalt or calcium at the exchangeable cationic sites. The adsorbents used in each stage may or may not have the same composition and if the composition is the same, the physically same adsorbent may or may not be utilized in both stages, however, it is preferred that the adsorbents used in each stage be physically distinct.

Cationic or base exchange methods are generally known to those familiar with the field of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. It is contemplated that cation exchange operations may take place using individual solutions of desired cations to be placed on the zeolite or using an exchange solution containing a mixture of cations, where two or more desired cations are to be placed on the zeolite.

Feed mixtures which can be utilized in the process of this invention will comprise a mixture of ortho, meta and para chloronitrobenzene. Mixtures containing quantities of each of these isomers may be produced by processes which are well known to the chemical arts. These isomers are separated by the adsorbents utilized in the process of this invention according to their configuration depending whether they are a para-, meta- or ortho-isomer construction. Specifically, the ortho-isomer is selectively adsorbed relative to the other isomers in a first adsorption stage and either the meta or para isomer is selectively adsorbed in a second adsorption stage.

To separate the ortho-isomer from a feed mixture containing the ortho-, meta- and para- isomers of chloronitrobenzene, the mixture is first contacted with an adsorbent comprising a crystalline aluminosilicate and the ortho-isomer is more selectively adsorbed and retained by the adsorbent while the other isomers are relatively unadsorbed and are removed from the interstitial void spaces between the particles of adsorbent and the surface of the adsorbent. The relatively unadsorbed isomers are then contacted with an adsorbent comprising a crystalline aluminosilicate and depending on the precise composition of such adsorbent, either the meta or para isomer is more selectively adsorbed and retained by the adsorbent while the other isomer is relatively unadsorbed and is removed from the interstitial void spaces between the particles of adsorbent and the surface of the adsorbent. An adsorbent containing a more selectively adsorbed isomer is referred to as a "rich" adsorbent—rich in the more selectively adsorbed isomer.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream from the first adsorption stage will contain as raffinate components all of the feed mixture isomers except the ortho-isomer and the extract stream will contain ortho-isomer as the extract component.

Although it is possible by the process of this invention to produce a high purity (98% or greater) isomer product at high recoveries, it will be appreciated that an extract component is never completely adsorbed by the adsorbent, nor is a raffinate component completely nonadsorbed by the adsorbent. Therefore, small amounts of raffinate component can appear in an extract stream, and, likewise, small amounts of an extract component can appear in a raffinate stream. The extract and raffinate streams then are further distinguished from each other and from the feed mixture by the ratio of the concentrations of an extract component and a specific raffinate component, both appearing in the particular stream. For example, in the first adsorption stage the ratio of concentration of the more selectively adsorbed ortho-isomer to the concentration of a less selectively adsorbed isomer will be highest in the extract stream, next highest in the feed mixture, and lowest in the raffinate stream. Likewise, the ratio of a less selectively adsorbed isomer to a more selectively adsorbed isomer will be highest in a raffinate stream, next highest in the feed mixture, and the lowest in an extract stream.

As mentioned above, the physically same adsorbent may be used in both adsorption stages. This would be accomplished by retaining the unadsorbed isomers from the first adsorption stage in, for example, a holding tank, until the ortho-isomer is desorbed and then contacting the adsorbent from which the ortho-isomer was desorbed with the isomers in the holding tank to effect the second desorption stage. It is preferred, however, to use physically distinct adsorbents for both stages for reasons of efficiency and continuity of operation.

The adsorbed isomer could be removed from the adsorbent by purging or increasing the temperature of the adsorbent or by decreasing the pressure of the chamber or vessel containing the adsorbent or by a combination of these means, however, it is preferred that the adsorbent be contacted with a desorbent material which is capable of displacing an adsorbed isomer from the adsorbent. The resultant extract stream comprising the dissolved isomer and desorbent material is subjected to a separation step so as to obtain high purity isomer.

The adsorbents may be employed in the form of dense compact fixed beds which are alternatively contacted with the feed mixture and desorbent materials. In the simplest embodiment of the invention, the adsorbents are employed in the form of single static beds in which case the process is only semi-continuous. In the preferred embodiment a set of two or more static beds for each adsorption stage may be employed in fixed-bed contacting with appropriate valving and programmed control so that the feed mixture to that stage is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred for use in my separation process. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passes from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent for each adsorption stage be located in a single column, the use of multiple chambers or a series of columns for each such stage is within the scope of the invention.

It is not necessary that all of the input or output streams be simultaneously used, and in fact, in many instances some of the streams can be shut off while others effect an input or output of material. The apparatus which can be utilized to effect the process of this invention can also, for each adsorption stage, contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan, on Apr. 2, 1969, for further explanation of the simulated moving-bed countercurrent process flow scheme.

Adsorption and desorption conditions for adsorptive separation processes can generally be either in the liquid or vapor phase or both but for aromatic isomer separation processes employing zeolitic adsorbents all liquid-phase operations are usually preferred because of the lower temperature requirements and the slightly improved selectivities associated with the lower temperatures. Preferred adsorption conditions for the process of this invention will include temperatures within the range of from about 70° F. to about 450° F. and will include pressures in the range from about atmospheric to about 500 psig. Pressures higher than about 500 psig. do not appear to affect the selectivity to a measurable amount and additionally would increase the cost of the process. Desorption conditions for the process of the invention shall generally include the same range of temperatures and pressures as described for adsorption operations. The desorption of the selectively adsorbed isomer could also be effected at subatmospheric pressures or elevated temperatures or both or by vacuum purging of the adsorbent to remove the adsorbed isomer but this process is not directed to these desorption methods.

The desorbent materials which can be used in the various processing schemes employing an adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed components from the adsorbent.

However, in adsorptive separation processes which employ zeolitic adsorbents and processes which are generally operated at substantially constant pressures and temperatures to insure liquid phase, the desorbent material relied upon must be judiciously selected to satisfy several criteria. First, the desorbent material must displace the adsorbed feed component from the adsorbent with reasonable mass flow rates without itself being so strongly adsorbed as to unduly prevent the extract component from displacing the desorbent material in a following adsorption cycle. Secondly, desorbent materials must be compatible with the particular adsorbent and the particular feed mixture. More specifically, they must not reduce or destroy the critical selectivity of the adsorbent for the extract component with respect to the raffinate components.

Desorbent materials to be used in the process of this invention should additionally be substances which are easily separable from components of the feed mixture that is passed into the process. In desorbing the preferentially adsorbed component of the feed, both desorbent material and the extract component are removed in admixture from the adsorbent. Without a method of separation such as distillation of these two materials, the purity of the extract component of the feed stock would not be very high since it would be diluted with desorbent. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture. An extract stream or raffinate stream from which the desorbent material has been separated and which is removed from the process as a desired product, is referred to as an "extract product" or "raffinate product" respectively. Preferred desorbent material for use in the process of this invention may be one compound or a mixture of compounds selected from the group consisting of nitrobenzene, toluene and 1-heptanol.

The adsorbents used in the process of my invention can be better understood by brief reference to certain adsorbent properties which are necessary to the successful operation of a selective adsorption process. It will be recognized that improvements in any of these adsorbent characteristics will result in an improved separation process. Among such properties are: adsorptive capacity for some volume of an extract component per volume of adsorbent, the selective adsorption of an extract component with respect to a raffinate component and the desorbent material, sufficiently fast rates of adsorption and desorption of the extract component to and from the adsorbent; and, in instances where the components of the feed mixture are very reactive, little or no catalytic activity for undesired reactions such as polymerization and isomerization.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed paraffinic tracer (n-$C_{14}$) and of isomers of chloronitrobenzene, all diluted in desorbent, is injected for a duration of several minutes. Desorbent flow is resumed, and the tracer and the isomers are eluted as in a liquid-solid chromatographic operation. The effluent is analyzed by on-stream chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate.

Selectivity (B), with regard to two given components, is equal to the quotient obtained by dividing the respective retention volume of such components. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 1.5 and particularly preferred that such selectivity be greater than 2.0. Like relative volatility, the higher the selectivity the easier the separation is to perform. Higher selectivities permit a smaller amount of adsorbent to be used.

The rate of exchange relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity or selectivity or product yields, or all of these, but in the adsorptive separation of aromatic hydrocarbon isomers with a zeolite-containing adsorbent this is generally not a problem.

To further evaluate promising adsorbent systems and to translate this type of data into a practical isomer separation process requires actual testing of the best system in a continuous countercurrent liquid-solid contacting device. The general operating principles of such a device have been previously described and are found in Broughton U.S. Pat. No. 2,985,589 and a specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on adsorbent testing and evaluation may be found in the paper "Separation $C_8$ Aromatics by Adsorption" by A. J. deRosset, R. W. Neuzil, A. J. Korous, and D. H. Rosback presented at the American Chemical Society, Los Angeles, California, Mar. 28–Apr. 2, 1971.

The example shown below is intended to further illustrate the process of this invention and is not to be construed as unduly limiting the scope and spirit of said process. The example presents pulse test results for various adsorbents.

EXAMPLE

In this example, four adsorbents were tested in a pulse test apparatus previously described to illustrate desired properties achieved by the process of this invention. The four adsorbents were tested using this test method to determine the selectivity of the adsorbent particles for ortho relative to the other chloronitrobenzene isomers and to determine the rate of desorption of ortho-chloronitrobenzene by a particular desorbent. The feed mixture used contained 10 vol. % para-chloronitrobenzene, 10 vol. % meta-chloronitrobenzene, 10 vol. % ortho-chloronitrobenzene, 5 vol. % of normal $C_{14}$ paraffin which was used as a tracer, and 65 vol. % of toluene. The desorbent employed was a blend of 50% nitrobenzene and 50% toluene. All of the adsorbents were dried in an open dish in a furnace for 1 hour at 500° C.

The dynamic testing apparatus was maintained at a controlled temperature of 150° C. with sufficient pressure on the entire testing unit to maintain essentially liquid phase operation. The sequence of operations for each test was: the desorbent was first continuously run through the column; at a convenient time desorbent flow was stopped; a 4.6 cc sample of feed was injected into the column via a sample loop; and the desorbent flow was resumed. The effluent from the column was constantly monitored with chromatographic equipment and traces of the envelopes of component peaks were developed. From these traces data can be obtained, in the manner previously described, which will characterize various adsorbent properties.

The results of the adsorptive testing for the four adsorbents are shown in Table No. I below.

TABLE I

Retention Volumes and Width of Peak Envelopes (At One-Half Intensity)

| Test | Adsorbent | Peak | Retention Volume | Peak Width |
|---|---|---|---|---|
| 1 | K-X | n-$C_{14}$ | 46.0 cc | 10.0 cc |
|  |  | p-CNB | 51.1 | 7.0 |
|  |  | m-CNB | 54.7 | 8.0 |
|  |  | o-CNB | 65.0 | 11.0 |
| 2 | K-Y | n-$C_{14}$ | 43.6 | 12.0 |
|  |  | p-CNB | 48.9 | 10.0 |
|  |  | m-CNB | 51.6 | 9.5 |
|  |  | o-CNB | 60.6 | 17.5 |
| 3 | Co-Y | n-$C_{14}$ | 48.1 | 11.1 |
|  |  | p-CNB | 54.5 | 9.5 |
|  |  | m-CNB | 56.1 | 9.5 |
|  |  | o-CNB | 58.3 | 10.5 |
| 4 | Ca-Y | n-$C_{14}$ | 48.0 | 10.3 |
|  |  | p-CNB | 56.3 | 9.5 |
|  |  | m-CNB | 55.4 | 9.5 |
|  |  | o-CNB | 58.5 | 9.5 |

From the retention volumes set forth in Table I, selectivities of interest were calculated and are set forth in Table II below.

TABLE II

Selectivity Indexes

| Adsorbent | Selectivities | | | |
|---|---|---|---|---|
|  | o/p | o/m | m/p | p/m |
| K-X | 3.72 | 2.18 | 1.70 | — |
| K-Y | 3.20 | 2.12 | 1.51 | — |
| Co-Y | 1.40 | 1.28 | 1.10 | — |
| Ca-Y | 1.26 | 1.42 | — | 1.12 |

As can be seen from the above data, all four adsorbents tested were preferentially selective for adsorbing ortho-chloronitrobenzene with respect to the other isomers. The K-X and K-Y adsorbents, however, exhibited a particularly high selectivity for the ortho isomer.

The selectivies of the K-X and K-Y adsorbents with respect to ortho-chloronitrobenzene are clearly advantageous and the rates of orthochloronitrobenzene adsorption-desorption for those adsorbents are not substantially greater than the rates for the Co-Y and Ca-Y adsorbents. As mentioned above, these rates are characterized by the width of the peak envelopes at half intensity of the isomers in question. The narrower the peak width, the faster the adsorption-desorption rate.

The K-X adsorbent is, therefore, particularly preferred for the separation of the ortho-isomer from a mixture of the three isomers of chloronitrobenzene and thus for use in at least the first adsorption stage of this invention, in view of its high selectivity for the ortho-isomer and an adsorption-desorption rate for that isomer not significantly less than any of the other adsorbents tested. The K-X adsorbent would also be particularly preferred for use in the second adsorption stage, in view of its having, in comparison with the other adsorbents, the highest selectivity for the meta isomer and at the same time the highest adsorption-desorption rate for the meta isomer as indicated by the meta isomer peak envelope width in Table I.

The following illustrative embodiment is presented to illustrate the flow scheme of my invention and is not intended to unduly restrict the scope and spirit of the claims attached hereto.

ILLUSTRATIVE EMBODIMENT AND DESCRIPTION OF THE DRAWING

The following illustrates my process when operated in a preferred embodiment, i.e. one which utilizes a continuous, simulated moving bed, countercurrent flow system in each adsorption stage with K-Y zeolite as the adsorbent in both stages. The adsorption stages are physically distinct.

Specifically, this embodiment presents a flow scheme with illustrative details as to operating conditions and stream compositions for a pilot-plant-scale testing apparatus as previously discussed, one of which is used for each adsorption stage. The particular device for use in this Example is known as a carousel unit, which is described in detail in deRosset et al U.S. Pat. No. 3,706,816 incorporated herein by reference. Briefly, the apparatus consists essentially of 24 serially connected adsorbent chambers having about 18.8 cc. volume each. Total chamber volume of the apparatus is approximately 450 cc. The individual adsorbent chambers are serially connected to each other with relatively small-diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids flow to and from the process. The rotary valve contains a feed input line through which passes a feed mixture containing an extract and a raffinate component, an extract stream outlet line through which passes desorbent material, in admixture with an extract component, a desorbent material inlet line through which passes desorbent material and a raffinate stream outlet line through which passes a raffinate component in admixture with desorbent material. Additionally, a flush material inlet line is used to admit flush material for the purpose of flushing feed components from lines which had previously contained feed material and which were to subsequently contain a raffinate or extract output stream. The flush material employed is desorbent material which leaves the apparatus as part of the extract and raffinate output streams.

The feed mixture is a mixture of 34 vol. % o-chloronitrobenzene, 65 vol. % p-chloronitrobenzene and 1 vol.

% m-chloronitrobenzene. The desorbent material used comprises a blend of 50% nitrobenzene and 50% toluene.

Now, with reference to the drawing, the feed mixture is passed via line 1 to adsorption column 2 which contains K-X adsorbent. The operating temperature for adsorption column 2 is 150° C. with sufficient pressure to maintain essentially liquid phase operation. Substantially all of the o-chloronitrobenzene is selectively adsorbed as extract in adsorption column 2. The desorbent material effecting desorption of the extract in adsorption column 2 is introduced thereto via line 9.

The first extract stream leaves adsorption column 2 via line 5 and passes thereby to fractionation 4 for removal of desorbent material. The extract product stream that leaves fractionation 4 via line 6 comprises substantially pure o-chloronitrobenzene.

The first raffinate stream which leaves adsorption column 2 via line 7 comprises, on a desorbent material free basis, 1.52 vol. % m-chloronitrobenzene and 98.48 vol. % p-chloronitrobenzene. This stream passes to fractionator 8 via line 7 for removal of a substantial portion of desorbent material therefrom.

The first raffinate stream of reduced desorbent material content passes from fractionator 8 via line 3 to adsorption column 10 which contains K-X adsorbent. The operating temperature for adsorption column 10 is 50° C. with sufficient pressure to maintain essentially liquid phase operation. Substantially all of the m-chloronitrobenzene is selectively adsorbed as extract in adsorption column 10. The desorbent material effecting desorption of the extract in adsorption column 10 is introduced thereto via line 11.

The second extract stream, comprising substantially pure m-chloronitrobenzene and desorbent material, leaves adsorption column 10 via line 12, and passes thereby to fractionator 13 for removal of desorbent material. The second extract product stream that leaves fractionator 13 via line 14 comprises substantially pure m-chloronitrobenzene.

The second raffinate stream which leaves adsorption column 10 via line 15 comprises substantially pure p-chloronitrobenzene and desorbent material. This stream passes to fractionator 16 via line 15 for removal of substantially all of the desorbent material therefrom. The raffinate product stream that leaves fractionator 16 via line 17 comprises substantially pure p-chloronitrobenzene.

Desorbent material leaves fractionators 8, 4, 13 and 16 via lines 18, 19, 20 and 21, respectively. The desorbent material for use in adsorption column 2 is recycled from fractionator 8 via lines 18 and 9, and from fractionator 4 via lines 19 and 9. The desorbent material for use in adsorption column 10 is recycled from fractionator 16 via lines 21 and 11, and from fractionator 13 via lines 20 and 11.

I claim as my invention:

1. A process for separating the ortho, meta and para isomers of chloronitrobenzene from a feed mixture comprising said isomers, which process comprises contacting in a first adsorption stage at adsorption conditions said mixture with an adsorbent comprising a type X or type Y zeolite containing at the exchangeable cationic sites one or more cations selected from the group consisting of Groups IA, IIA and the transition metals of the Periodic Table of Elements, selectively adsorbing the ortho-isomers to the substantial exclusion of the meta and para isomers, recovering high-purity ortho-chloronitrobenzene as a first extract product and said meta and para isomers as a raffinate stream, contacting in a second adsorption stage at adsorption conditions said raffinate stream with an adsorbent selective for either said meta or para isomer and comprising a type X or type Y zeolite containing at the exchangeable cationic sites one or more cations selected from the group consisting of Group IA, IIA and the transition metals of the Periodic Table of Elements, selectively adsorbing said meta or para isomer as the selected isomer, to the substantial exclusion of the non-selected isomer and recovering high-purity selected isomer as a second extract product and high-purity non-selected isomer as a raffinate product.

2. The process of claim 1 further characterized in that the adsorbent used in said second adsorption stage is physically the same adsorbent used in said first adsorbent stage.

3. The process of claim 1 further characterized in that the adsorbent used in said first adsorption stage is physically distinct from the adsorbent used in the second adsorption stage.

4. The process of claim 1 further characterized in that said zeolite in one or both of said adsorption stages, is essentially completely exchanged with potassium.

5. The process of claim 1 further characterized in that said zeolite in one or both of said adsorption stages is essentially completely exchanged with calcium.

6. The process of claim 1 further characterized in that said zeolite in one or both of said adsorption stages is essentially completely exchanged with cobalt.

7. The process of claim 1 including the step of treating the adsorbents containing adsorbed isomers with desorbent material to remove said isomers therefrom as fluid extract streams.

8. The process of claim 7 further characterized in that said desorbent material has an average boiling point substantially different from that of the feed mixture.

9. The process of claim 8 further characterized in that said desorbent material comprises one compound or a mixture of compounds selected from the group consisting of nitrobenzene, toluene and 1-heptanol.

* * * * *